(12) United States Patent
Zhang et al.

(10) Patent No.: US 9,354,163 B2
(45) Date of Patent: May 31, 2016

(54) METHODS TO INCREASE THE NUMBER OF FILTERS PER OPTICAL PATH IN A DOWNHOLE SPECTROMETER

(75) Inventors: Wei Zhang, Houston, TX (US); Robert Atkinson, Richmond, TX (US); Michael T. Pelletier, Houston, TX (US); Christopher M. Jones, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 22 days.

(21) Appl. No.: 14/117,542

(22) PCT Filed: May 24, 2011

(86) PCT No.: PCT/US2011/037655
§ 371 (c)(1),
(2), (4) Date: Nov. 13, 2013

(87) PCT Pub. No.: WO2012/161693
PCT Pub. Date: Nov. 29, 2012

(65) Prior Publication Data
US 2014/0070083 A1    Mar. 13, 2014

(51) Int. Cl.
| | |
|---|---|
| *G01V 5/00* | (2006.01) |
| *G01N 21/25* | (2006.01) |
| *G01J 3/12* | (2006.01) |
| *G01J 3/51* | (2006.01) |
| *G02B 26/00* | (2006.01) |
| *G01V 8/00* | (2006.01) |
| *G01J 3/02* | (2006.01) |

(52) U.S. Cl.
CPC ............. *G01N 21/255* (2013.01); *G01J 3/0202* (2013.01); *G01J 3/12* (2013.01); *G01J 3/51* (2013.01); *G01V 8/00* (2013.01); *G02B 26/008* (2013.01); *G01J 2003/1221* (2013.01)

(58) Field of Classification Search
CPC ...................................................... G02B 26/008
See application file for complete search history.

(56) References Cited

U.S. PATENT DOCUMENTS

| | | | |
|---|---|---|---|
| 3,659,945 A | 5/1972 | Roche et al. | |
| 3,770,355 A * | 11/1973 | Anthon ................ | G01M 11/00 250/339.07 |

(Continued)

FOREIGN PATENT DOCUMENTS

WO    WO-2012/161693    11/2012

OTHER PUBLICATIONS

PCT International Search Report and Written Opinion, dated Oct. 28, 2011, Appl No. PCT/US2011/037655, "Methods to Increase the Number of Filters Per Optical Path in a Downhole Spectrometer", filed May 24, 2011, 10 pgs.

(Continued)

*Primary Examiner* — Kiho Kim
(74) *Attorney, Agent, or Firm* — Krueger Iselin LLP; Benjamin Fite

(57) ABSTRACT

Downhole spectrometer tools are provided with two ways to increase the number of filters on an optical path. A first approach employs multiple filter wheels that rotate alternately in a common plane to intersect the optical path. Portions of the wheels are cut out to avoid mechanical interference between the wheels. A second approach drives the one or more filter wheels with a wobble that causes the filters to trace one or more hypocycloidal curves that each intersect the optical path.

30 Claims, 4 Drawing Sheets

(56) References Cited

U.S. PATENT DOCUMENTS

| | | | |
|---|---|---|---|
| 4,217,040 A | | 8/1980 | Longerbeam |
| 5,650,832 A | * | 7/1997 | Poradish et al. .............. 348/743 |
| 6,543,281 B2 | | 4/2003 | Pelletier et al. |
| 6,729,398 B2 | | 5/2004 | Ringgenberg et al. |
| 7,336,356 B2 | | 2/2008 | Vannuffelen et al. |
| 7,784,350 B2 | | 8/2010 | Pelletier |
| 7,938,175 B2 | | 5/2011 | Skinner et al. |
| 7,958,936 B2 | | 6/2011 | McGregor et al. |
| 8,037,935 B2 | | 10/2011 | Pelletier |
| 8,367,413 B2 | | 2/2013 | Jones et al. |
| 8,427,638 B2 | | 4/2013 | Atkinson et al. |
| 2003/0142241 A1 | * | 7/2003 | Allen et al. .................. 348/742 |
| 2003/0223069 A1 | | 12/2003 | DiFoggio et al. |
| 2008/0106703 A1 | | 5/2008 | Miyazawa |
| 2011/0108719 A1 | | 5/2011 | Ford et al. |
| 2011/0108720 A1 | | 5/2011 | Ford et al. |
| 2011/0108721 A1 | | 5/2011 | Ford et al. |

OTHER PUBLICATIONS

International Preliminary Report on Patentability, dated Jun. 13, 2013, Appl No. PCT/US2011/037655, "Methods to Increase the Number of Filters Per Optical Path in a Downhole Spectrometer", filed May 24, 2011, 23 pgs.

CA First Office Action, dated Sep. 4, 2014, Appl No. 2,837,171, "Methods to Increase the Number of Filters Per Optical Path in a Downhole Spectrometer," Filed May 24, 2011, 10 pgs.

* cited by examiner

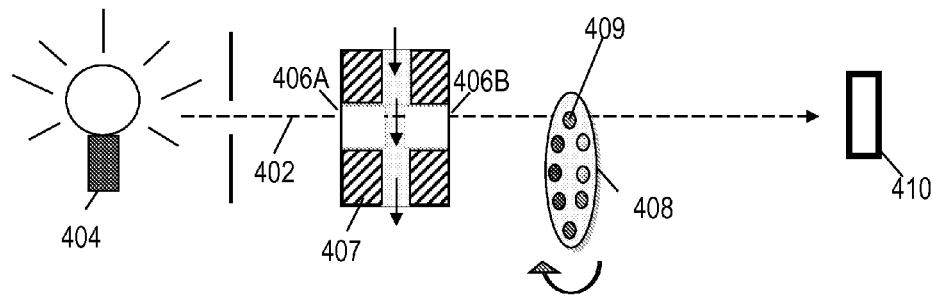
FIG. 4
FIG. 5
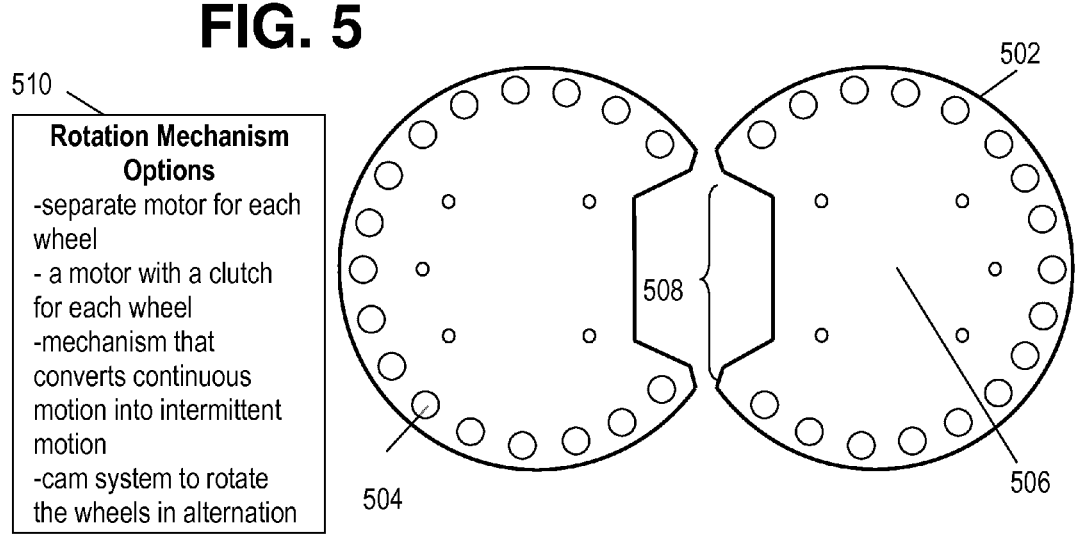
510
Rotation Mechanism Options
-separate motor for each wheel
- a motor with a clutch for each wheel
-mechanism that converts continuous motion into intermittent motion
-cam system to rotate the wheels in alternation
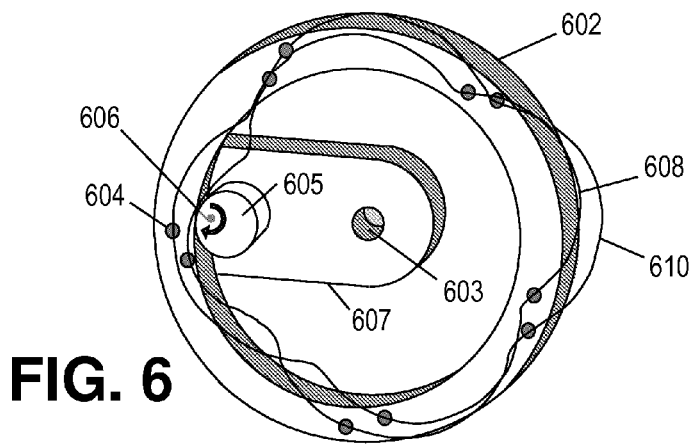
FIG. 6

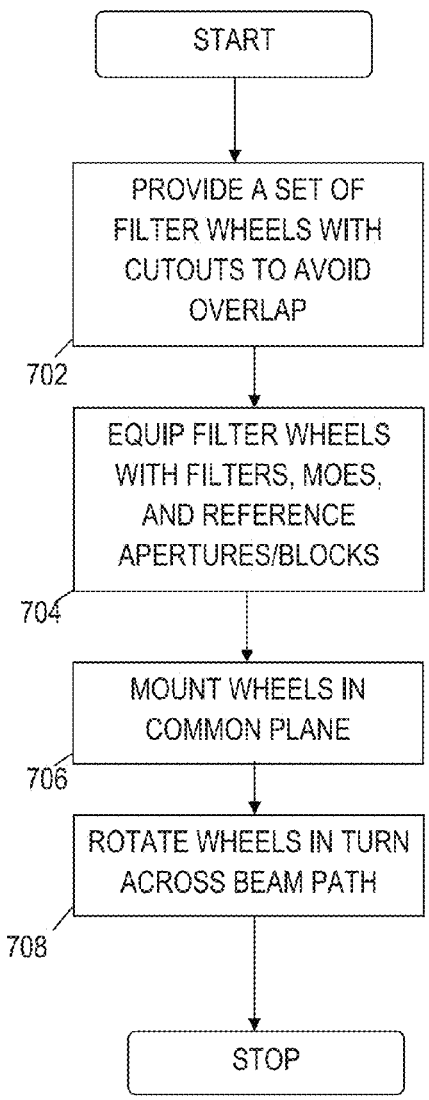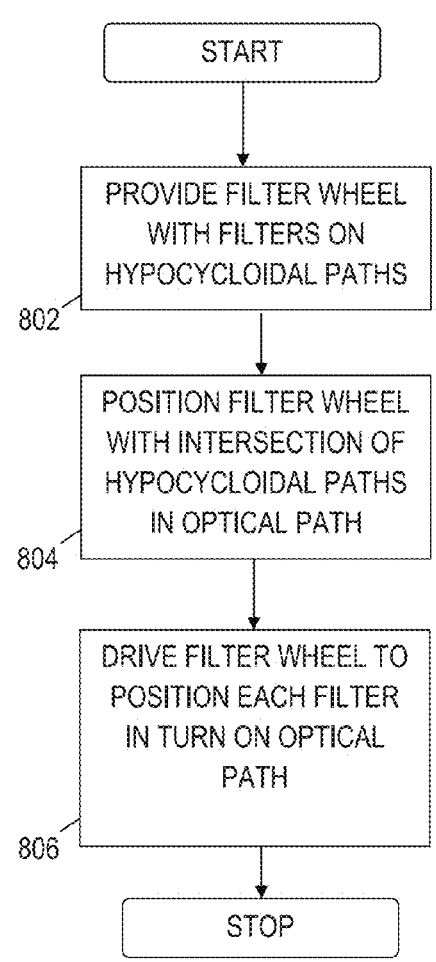

METHODS TO INCREASE THE NUMBER OF FILTERS PER OPTICAL PATH IN A DOWNHOLE SPECTROMETER

BACKGROUND

Engineers use downhole spectrometers to monitor, analyze, or identify different properties of fluid, such as contamination, composition, fluid type, and PVT ("pressure, volume, temperature") properties. For example, a spectrometer may be coupled to a formation fluid sampling tool to analyze fluids in real time as they are drawn from the formation. During the sampling operation the spectrometer can monitor contamination levels from borehole fluids and, once the contamination has fallen to an acceptable level, the spectrometer can measure spectral characteristics of the formation fluid to identify its components. Fluid component identification is helpful for determining whether and how production should be performed from a particular area of the well. It can provide indications of reservoir continuity, blowout risk, production value, etc.

Despite the evident utility of downhole spectrometers, the range of measurements that can be made by existing tools is somewhat limited. In the case of filter wheel spectrometers, this limitation is primarily due to spatial constraints on the filter wheel itself.

BRIEF DESCRIPTION OF THE DRAWINGS

FIG. 4 shows an illustrative spectrometer system;

FIG. 5 shows an illustrative double filter wheel configuration;

FIG. 6 shows an illustrative hypocycloidal filter wheel configuration;

FIG. 7 is a flow diagram of an illustrative first method for increasing a number of filters in a downhole spectrometer; and FIG. 8 is a flow diagram of an illustrative second method for increasing a number of filters in a downhole spectrometer.

TERMINOLOGY

A hypocycloid is sometimes defined as a shape drawn out by a fixed point on a small circle as it rotates inside a larger circle. However, as the term "hypocycloid" is used herein, it includes the shapes drawn by any point fixed relative to a first circle as it rotates inside or outside a second circle of smaller or larger diameter. Specific examples of such shapes elsewhere termed epicycloids, epitrochoids, and hypotrochoids, are included within the scope of this term as used in the present specification and claims.

The term "fluid" as used herein includes both liquids and gases.

DETAILED DESCRIPTION

The issues identified in the background are at least in part addressed by the disclosed methods for increasing the number of filters per optical path in a downhole spectrometer. Embodiments of a first method employ a set of filter wheels in a common plane that intersects an optical path. Each of the wheels is provided with a shape that permits rotation of the individual wheels without mechanically interfering with the other wheel(s) in the set. Embodiments of a second method employ a drive mechanism that causes points on the filter wheel to trace out hypocycloidal paths. The filters in the wheel are arranged so that their corresponding paths each intersect with the optical path. Some downhole spectrometer tools may employ both methods so that of multiple filter wheels is driven with the hypocycloidal drive mechanism.

Figure 1:
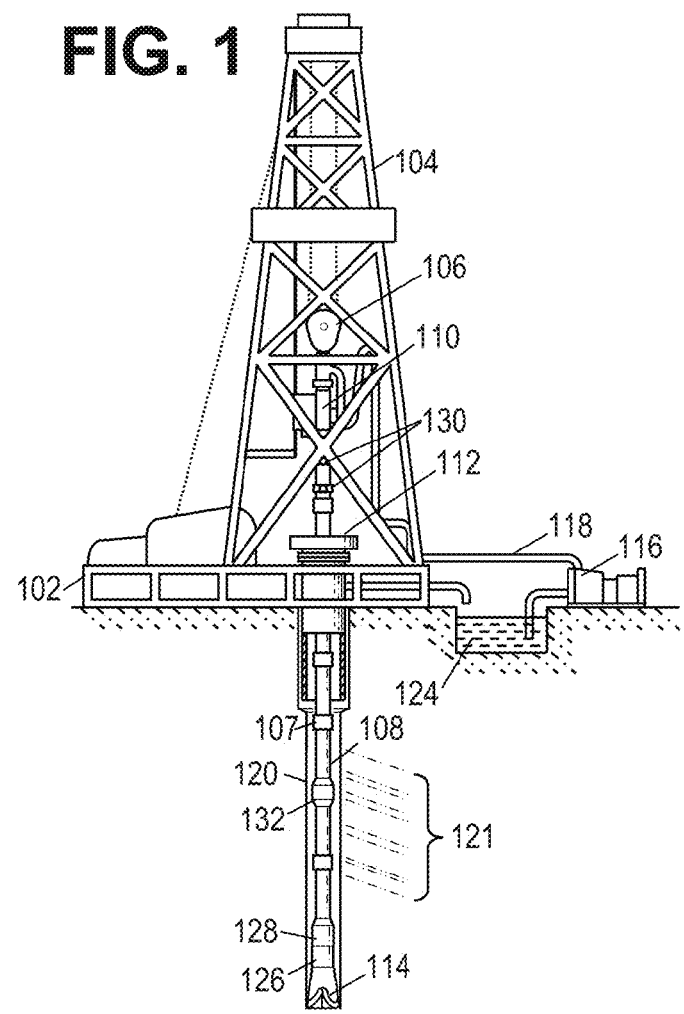
FIG. 1 shows an illustrative logging while drilling environment.

To further assist the reader's understanding of the disclosed systems and methods, we describe a suitable environment for their use and operation. Accordingly, FIG. 1 shows an illustrative logging while drilling (LWD) environment. A drilling platform 102 is equipped with a derrick 104 that supports a hoist 106 for raising and lowering a drill string 108. The hoist 106 suspends a top drive 110 that is used to rotate the drill string 108 and to lower the drill string through the well head 112. Sections of the drill string 108 are connected by threaded connectors 107. Connected to the lower end of the drill string 108 is a drill bit 114. As bit 114 rotates, it creates a borehole 120 that passes through various formations 121. A pump 116 circulates drilling fluid through a supply pipe 118 to top drive 110, downhole through the interior of drill string 108, through orifices in drill bit 114, back to the surface via the annulus around drill string 108, and into a retention pit 124. The drilling fluid transports cuttings from the borehole into the pit 124 and aids in maintaining the integrity of the borehole 120.

Figure 2:
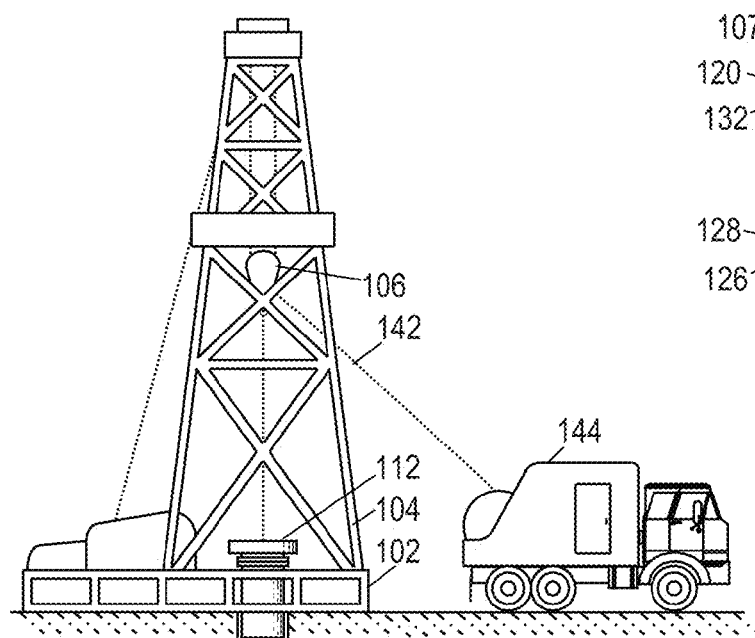
FIG. 2 shows an illustrative wireline logging environment.
Figure 2:
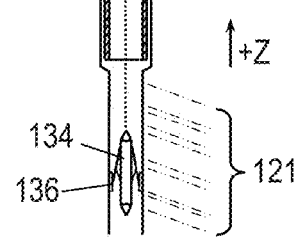

FIG. 2 shows an illustrative wireline logging environment. At various times during the drilling process, the drill string 108 is removed from the borehole to allow the use of a wireline logging tool 134. The wireline logging tool is a sensing instrument sonde suspended by a cable 142 having conductors for transporting power to the tool and telemetry from the tool to the surface. The wireline logging tool 134 may have arms 136 that center the tool within the borehole or, if desired, press the tool against the borehole wall. A logging facility 144 collects measurements from the logging tool 134, and includes computing facilities for processing and storing the measurements gathered by the logging tool.

Figure 3:
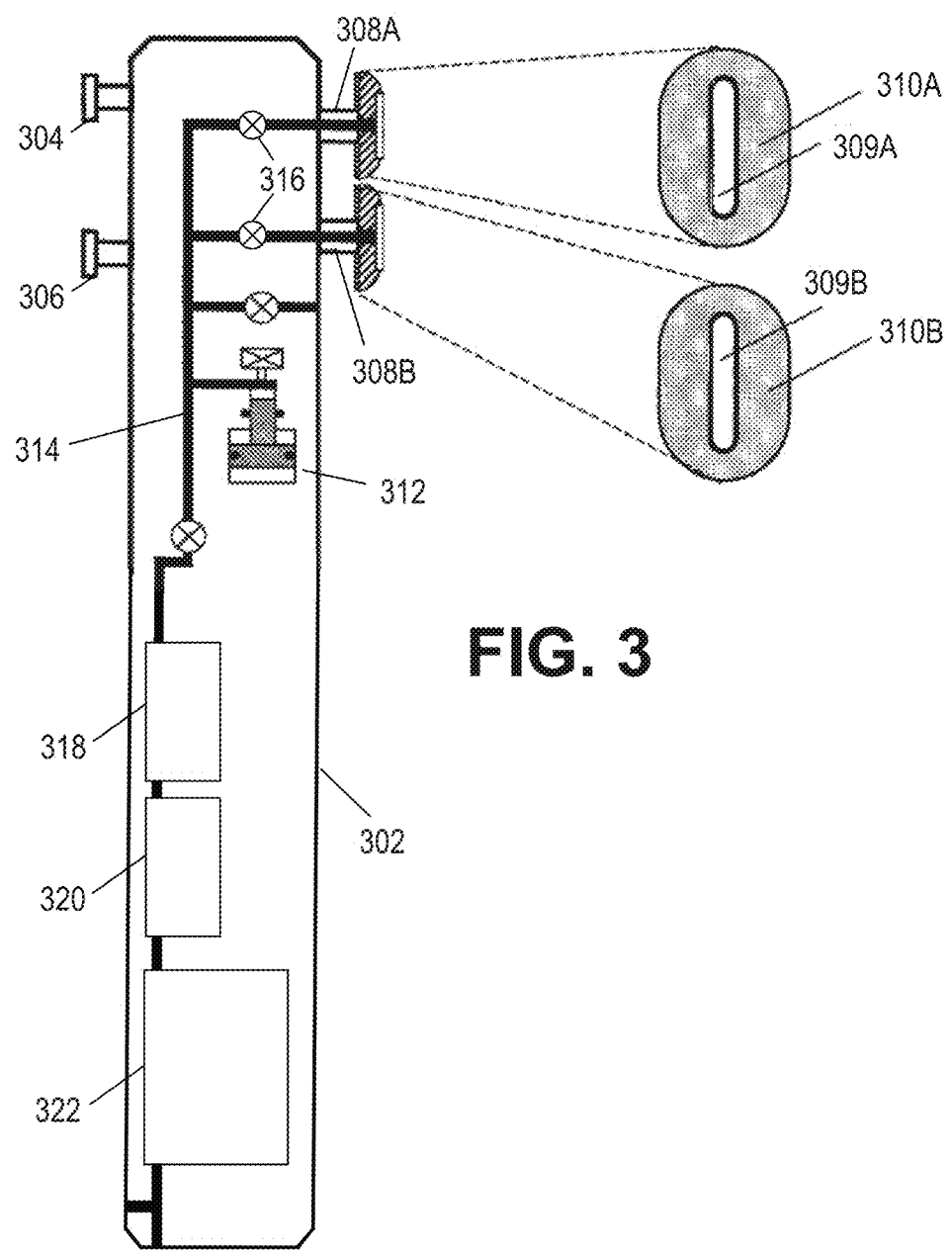
FIG. 3 shows an illustrative formation sampling tool with a downhole optical fluid analyzer.

A downhole optical fluid analyzer can be employed to characterize downhole fluids in both of the foregoing logging environments. For example, FIG. 3 shows an illustrative formation fluid sampling tool 302 for use in a wireline environment. The formation fluid sampling tool 302 includes one or more cup-shaped sealing pads for contacting the formation, one or more spectrometers, and a multi-chamber sample collection cassette. Arms 304 and 306 are extended from the side of tool 302 to contact the borehole wall and force the tool to the opposite side of the borehole, where sealing pads 310A and 310B (with slits 309A and 309B) make contact to the formation. Probes 308A and 308B are coupled to a piston pump 312 to draw formation fluid samples in from the formation via slits 309A, 309B. With the cooperation of valves 316, the piston pump 312 regulates the flow of various fluids in and out of the tool via a flow line 314. Ultimately, the fluid samples are exhausted to the borehole or captured in one of the sample collection module's 322 sample chambers. The illustrated tool further includes two optical analyzers 318 and 320 to perform in-situ testing of fluid samples as they travel along flow line 314.

FIG. 4 schematically illustrates the operating principles of a downhole filter wheel optical fluid analyzer. A light source 404 such as a tungsten filament, a halogen bulb, a fluorescent bulb, a laser, a light-emitting diode, etc., emits light along a light path 402. The illustrated light path 402 is shown as a straight line, but it may be defined in more complex ways using, e.g., apertures, mirrors, waveguides, fibers, lenses, prisms, and gratings. Light traveling along path 402 shines through a sample cell 407 via a first optically transparent window 406a, through the fluid, and then out a second window 406b. The fluid interacts with the light, thereby imprinting its spectral fingerprint on the light spectrum. As the light continues along the light path 402 it interacts with filters 409 in a rotating filter wheel before reaching a light detector 410. Various forms of light detectors are suitable for measuring light intensity include photodetectors and thermal detectors.

Aside from optional calibration elements such as an open aperture or a fully opaque light stop, the filters 409 are chosen to measure particular spectral characteristics suitable for identifying or otherwise characterizing the contents of the sample cell. As such, the filters may include bandpass filters, bandstop filters, and multivariate optical elements (MOE). The intensity of the light striking the detector is thus a measure of some portion of the spectral fingerprint mentioned previously. To ensure an adequate signal-to-noise ratio, the filters must be larger or equal to some given size that is a function of the manufacturing specifications for the other components (e.g., light source intensity, detector sensitivity, wheel rotation rate, and sample cell size). Moreover, the filter wheel has a limited circumference within which the filters must be placed, thereby limiting the number of filters that can be positioned in a given wheel.

To address this limitation, at least some of the disclosed downhole tool embodiments employ multiple filter wheels. Because the tool design generally requires that all of the filters intercept the optical path at a given position, the multiple filter wheels are located in a common plane as illustrated in FIG. 5. FIG. 5 illustrates an embodiment where two filter wheels 502 share an optical path passing midway between them. Each filter wheel 502 has evenly spaced filters 504 around its outer circumference. The shape of each filter wheel provides an omitted segment 508 to provide a clear path for rotation of the other filter wheel. The omitted segment can take a variety of shapes, from an arc that closely matches the path taken by the other wheel, to a shape that eliminates most of the interior area of the wheel to minimize weight. Other considerations to be taken into account are adequate rigidity, mounting stability, and ease of manufacturing. The filter wheels 502 rotate alternately, each turning a full rotation to clear the way for the rotation of the other. As each filter reaches the optical path, the filter wheel rotation may be paused momentarily to enable longer measurements.

Existing filter wheel designs for downhole optical fluid analyzers employ a filter wheel diameter of 3.188 inches which is sufficient to hold 20 filters, of which one may be an open aperture for calibration. It is expected that the omitted area for filter wheels in the two-wheel design will reduce the number of filters around the circumference to 17, thereby increasing the total number of filters to 34. Calibration can be performed when both wheels are clear from the optical path, eliminating the need for a calibration aperture in one of the filter positions. In this case, the two wheel design yields a 79% increase in the number of usable filters, without requiring the use of a beam splitter or optical switch that would decrease light intensity and/or reduce the tool's reliability in a downhole environment.

The two-wheel design can be extended to employ three or more filter wheels, each having an omitted segment to enable the rotation of each of the other wheels. As the number of filter wheels grows, so too does the size of each wheel's omitted segment, thereby limiting the amount of gains that can be made in this way.

A number of mechanisms (represented by rotation mechanism options block 510) may be employed to rotate the filter wheels 502. Some embodiments employ a separate electric motor is provided to drive each filter wheel. While having an advantage of implementation ease, it is expected that powering electrical motors in an on/off fashion reduces battery life and reduces reliability of the tool. Accordingly, a continuously-running electrical motor may be employed with two clutches to drive the wheels in alternation. Alternatively, a cam assembly or intermittent drive mechanism (such as a variant of a Geneva drive) can be employed to convert the continuous motion of the electrical motor into alternate rotations of the wheels.

Another way to increase the number of filters in a downhole spectrometer is to employ a filter wheel drive mechanism that causes points on the filter wheel to trace out hypocycloidal paths. Because the filter wheel "wobbles", the curve traced on the wheel by the optical path has a substantially greater length than the circumference of the wheel, thereby enabling the use of a greater number of filters on one wheel than would otherwise be possible. FIG. 6 shows one potential drive mechanism having a wheel 602 that turns on an axis that passes through hole 603 in sliding plate 607. An eccentric gear 605 turns about axis 606, causing the sliding plate 607 to oscillate back and forth as the gear 605 turns the wheel 602. The illustrated wheel diameters have a 5/1 ratio, causing the inner wheel to rotate five times for each single concurrent rotation of the outer wheel and thereby causing each of the filters to follow one of the illustrated hypocycloidal curves 608, 610. The inner five filters follow curve 608, while the outer five filters follow curve 610. The optical path is located at one of the intersections between curves 608, 610, so that each of the filters will pass in turn through the optical path. However, the number of filters on each row is not limited to five. Contemplated embodiments include a large number of filters. In addition, at least some contemplated embodiments include more than two hypocycloid curves.

Other ratios and wheel configurations can be employed to vary the number and size of lobes in the hypocycloidal curves traced out by the filters. In each case, the wheel's wobble enables filters placed at multiple radial distances from the wheel's axis to still pass through the optical path. Moreover, the hypocycloidal drive mechanism can be employed for each of multiple filter wheels in a common plane so as to further increase the number of filters in the downhole spectrometer.

FIG. 7 is a flow diagram for the first illustrative method for increasing the number of filters per optical path in a downhole spectrometer tool. In block 702, the tool manufacturer shapes a set of filter wheels, each with an omitted section to permit interference-free rotation of the wheels relative to each other. In block 704, each of the filter wheels is equipped with filter elements such as, e.g., calibration apertures, multivariate optical elements, and/or bandpass filters. In block 706, the manufacturer mounts the filter wheels in a common plane, with the wheel assembly centers on the tool's optical path. In block 708, the filter wheels rotate in turn across the optical path that includes a source, detector, and a fluid sample cell. While each wheel rotates, the others are held until the wheel completes a full rotation to re-open access to the optical path. As each filter enters the optical path, some tool embodiments may provide a brief pause to enable a longer measurement period.

FIG. 8 is a flow diagram for the second illustrative method for increasing the number of filters per optical path in a downhole spectrometer tool. In block 802, the tool manufacturer creates a filter wheel having filter elements positioned so that as they follow hypocycloidal paths, their paths will all intersect at one or more common points. In block 804, the manufacturer mounts the filter wheel in the downhole tool with the common intersection point aligned on the optical path. In block 806, the hypocycloidal drive mechanism turns the wheel to bring each filter in turn onto the optical path. Some embodiments may briefly pause as each filter occupies the optical path to enable a longer measurement period.

Numerous variations and modifications will become apparent to those skilled in the art once the above disclosure is fully appreciated. For example, the filter elements can be either transmissive or reflective filters, and the filter wheels can precede or follow the sample cell. It is intended that the following claims be interpreted to embrace all such variations and modifications.

What is claimed is:

1. A method for increasing the number of optical filters in a downhole spectrometer, the method comprising:
    providing a set of filter wheels on a common plane to intersect an optical path, wherein each of said wheels has an omitted segment that provides a clearance that permits rotation of individual wheels without interference; and
    rotating said individual wheels in turn to pass filters from each wheel across said optical path, said rotating causing a filter from a first wheel of the set to trace a first path that intersects, within said common plane, a second path traced by a filter from a second wheel of the set.

2. The method of claim 1, wherein said set of filter wheels has no more than two wheels.

3. The method of claim 1, wherein said rotating employs a separate motor for each wheel.

4. The method of claim 1, wherein said rotating employs a motor with a clutch for each wheel.

5. The method of claim 1, wherein said rotating employs a mechanism that converts continuous motion into intermittent motion.

6. The method of claim 1, wherein said rotating employs a cam system to rotate the wheels in alternation.

7. The method of claim 1, further comprising passing light through a downhole sample cell on the optical path.

8. The method of claim 1, wherein the rotations of said individual wheels in turn occur without transverse movement of the wheels in between the rotations.

9. A method for increasing the number of optical filters in a downhole spectrometer, the method comprising:
    driving an inner filter wheel with a mechanism that causes individual points to trace out hypocycloidal paths as a result of concurrent rotation of the inner filter wheel and an outer wheel having a diameter larger than a diameter of the inner filter wheel; and
    arranging filters on the inner filter wheel so that their corresponding hypocycloidal paths each intersect each other on an optical path.

10. The method of claim 9, wherein said filters are at two or more radial distances from a center of the inner filter wheel.

11. The method of claim 9, wherein the hypocycloidal paths are epicycloidal.

12. The method of claim 9, wherein the hypocycloidal paths are epitrochoids.

13. The method of claim 9, wherein the filters trace out no more than two hypocycloidal paths.

14. The method of claim 9, wherein the filters trace out at least three hypocycloidal paths.

15. The method of claim 9, further comprising passing light through a downhole sample cell on the optical path.

16. The method of claim 9, further comprising driving said filter wheel with a motion that causes said filters to each cross the optical path.

17. A downhole spectrometer tool that comprises:
    a downhole sample cell having a fluid sample;
    a filter wheel that turns around an inner or outer circumference of an outer gear to move its filters along hypocycloidal curves as a result of concurrent rotation of the filter wheel and the outer gear, the outer gear having a diameter larger than a diameter of the filter wheel; and
    an optical path through the sample cell and an intersection of the hypocycloidal curves.

18. The tool of claim 17, wherein the filter wheel has filters at two or more radial distances from its center.

19. The tool of claim 17, wherein said curves are epicycloids, epitrochoids, or hypotrochoids.

20. The tool of claim 17, wherein the filter wheel moves its filters along no more than two curves.

21. The tool of claim 17, wherein the filter wheel moves its filters along at least three curves.

22. The tool of claim 17, further comprising a second filter wheel, wherein both filter wheels rotate through the optical path on a common plane.

23. A downhole spectrometer tool that comprises:
    a downhole sample cell having a fluid sample;
    a set of filter wheels on a common plane to intersect an optical path, wherein each of said wheels has an omitted segment that provides a clearance that permits rotation of individual wheels without interference; and
    a rotation mechanism that rotates the individual wheels in turn to pass filters from each wheel across said optical path, wherein the rotation mechanism causes a filter from a first wheel of the set to trace a first path that intersects, within said common plane, a second path traced by a filter from a second wheel of the set.

24. The tool of claim 23, wherein the rotation mechanism comprises a separate motor for each wheel.

25. The tool of claim 23, wherein the rotation mechanism comprises a motor with a clutch for each wheel.

26. The tool of claim 23, wherein the rotation mechanism converts continuous motion into intermittent motion.

27. The tool of claim 23, wherein the rotation mechanism comprises a cam system to rotate the wheels in alternation.

28. The tool of claim 23, wherein the rotation mechanism causes each wheel of the set to complete a full rotation while other wheels of the set are held.

29. The tool of claim 23, wherein the rotation mechanism pauses as each filter enters the optical path.

30. The tool of claim 23, wherein each individual wheel of the set includes a plurality of spaced filters around its circumference.

* * * * *